US012692209B2

(12) United States Patent
Kobayashi et al.

(10) Patent No.: US 12,692,209 B2
(45) Date of Patent: Jul. 28, 2026

(54) HYDROCARBON PRODUCTION METHOD

(71) Applicant: ENEOS Corporation, Tokyo (JP)

(72) Inventors: Atsushi Kobayashi, Tokyo (JP); Akira Goto, Tokyo (JP); Takuya Kajita, Tokyo (JP)

(73) Assignee: ENEOS CORPORATION, Tokyo (JP)

( * ) Notice: Subject to any disclaimer, the term of this patent is extended or adjusted under 35 U.S.C. 154(b) by 543 days.

(21) Appl. No.: 18/251,947

(22) PCT Filed: Dec. 24, 2021

(86) PCT No.: PCT/JP2021/048172
§ 371 (c)(1),
(2) Date: May 5, 2023

(87) PCT Pub. No.: WO2022/138910
PCT Pub. Date: Jun. 30, 2022

(65) Prior Publication Data
US 2024/0002314 A1     Jan. 4, 2024

(30) Foreign Application Priority Data

Dec. 25, 2020     (JP) ................................. 2020-217587

(51) Int. Cl.
*C07C 1/04* (2006.01)
*B01D 53/02* (2006.01)
(Continued)

(52) U.S. Cl.
CPC .............. *C07C 1/044* (2013.01); *B01D 53/02* (2013.01); *B01D 53/229* (2013.01); *B01J 23/78* (2013.01);
(Continued)

(58) Field of Classification Search
None
See application file for complete search history.

(56) References Cited

U.S. PATENT DOCUMENTS 5,234,768 A     8/1993 Furuya
5,846,295 A     12/1998 Kalbassi et al.
(Continued)

FOREIGN PATENT DOCUMENTS

CN     107429410 A     12/2017
JP     H01-205088 A     8/1989
(Continued)

OTHER PUBLICATIONS

Office Action (Notification of Reason(s) for Refusal) issued on May 20, 2025, in corresponding Japanese Patent Application No. 2022-571677 and machine English translation of the Office Action. (9 pages).
(Continued)

*Primary Examiner* — Medhanit W Bahta
(74) *Attorney, Agent, or Firm* — BUCHANAN, INGERSOLL & ROONEY PC

(57) ABSTRACT

The hydrocarbon production method includes a first production step of producing carbon monoxide using carbon dioxide contained in source gas, and a second production step of producing hydrocarbon using hydrogen contained in source gas and carbon monoxide. The source gas contains at least one of carbon dioxide, carbon monoxide, and hydrogen not derived from fossil fuel.

17 Claims, 1 Drawing Sheet

(51) Int. Cl.

| *B01D 53/22* | (2006.01) |
| *B01J 23/72* | (2006.01) |
| *B01J 23/745* | (2006.01) |
| *B01J 23/78* | (2006.01) |
| *B01J 23/80* | (2006.01) |
| *B01J 37/00* | (2006.01) |
| *B01J 37/03* | (2006.01) |
| *C01B 32/40* | (2017.01) |
| *C10G 2/00* | (2006.01) |
| *C10K 3/02* | (2006.01) |
| *C25B 1/04* | (2021.01) |
| *C25B 15/08* | (2006.01) |

(52) U.S. Cl.

CPC ........... *B01J 23/80* (2013.01); *B01J 37/0009* (2013.01); *B01J 37/03* (2013.01); *C01B 32/40* (2017.08); *C07C 1/04* (2013.01); *C10G 2/332* (2013.01); *C10K 3/026* (2013.01); *C25B 1/04* (2013.01); *C25B 15/08* (2013.01); *C25B 15/081* (2021.01); *B01D 2256/24* (2013.01); *B01D 2257/108* (2013.01); *B01D 2257/502* (2013.01); *B01D 2257/504* (2013.01); *B01J 23/72* (2013.01); *B01J 23/745* (2013.01); *C07C 2523/745* (2013.01); *Y02E 60/36* (2013.01); *Y02P 20/133* (2015.11)

(56) References Cited

U.S. PATENT DOCUMENTS

| 2010/0137457 | A1 | 6/2010 | Kaplan |
| 2012/0123001 | A1 | 5/2012 | Mamedov et al. |
| 2018/0050330 | A1* | 2/2018 | Ishitani ................. C07D 213/61 |
| 2019/0359894 | A1* | 11/2019 | Heidel ................... B01J 19/245 |
| 2022/0305474 | A1 | 9/2022 | Ishitani |

FOREIGN PATENT DOCUMENTS

| JP | H0780309 | A | 3/1995 |
| JP | H11518 | A | 1/1999 |
| JP | 2006-297286 | A | 11/2006 |
| JP | 2008248179 | A | 10/2008 |
| JP | 2012140382 | A | 7/2012 |
| JP | 2012520384 | A | 9/2012 |
| JP | 2015051954 | A | 3/2015 |
| JP | 2015160186 | A | 9/2015 |
| JP | 2018-202332 | A | 12/2018 |
| JP | 2020121944 | A | 8/2020 |
| JP | 2021195316 | A | 12/2021 |
| WO | 2016136433 | A1 | 9/2016 |
| WO | 2017169195 | A1 | 10/2017 |

OTHER PUBLICATIONS

Dorner et al., "Influence of Gas Feed Composition and Pressure on the Catalytic Conversion of CO2 to Hydrocarbons Using a Traditional Cobalt-Based Fischer-Tropsch Catalyst" The American Chemical Society, 2009, pp. 4190-4195.

Haruna et al., "Pressure Swing Adsorption", J. Vac. Soc. Jpn., Dec. 20, 2000, vol. 43, No. 12, with English translation, pp. 1088-1093.

International Preliminary Report on Patentability (PCT/IB/373) mailed Jun. 13, 2023 and Written Opinion (PCT/ISA/237) mailed Mar. 8, 2022 both with English translations, in corresponding Patent Application No. PCT/JP2021/048172.

International Search Report (PCT/ISA/210) with English translation mailed on Mar. 8, 2022, by the Japanese Patent Office as the International Searching Authority for International Application No. PCT/JP2021/048172.

Extended European Search Report issued on Oct. 15, 2024, in corresponding European Patent Application No. 21911047.5. (9 pages).

Kaiser et al., "Production of Liquid Hydrocarbons With CO 2 As Carbon Source Based On Reverse Water-Gas Shift and Fischer-Tropsch Synthesis", Chemie Ingenieur Technik, vol. 85, No. 4, (Apr. 6, 2013), pp. 489-499, XP055297645.

Mohammad et al., "Reduced Graphene Oxide Supported Gold Nanoparticles for Electrocatalytic Reduction of Carbon Dioxide", Journal of Nanoparticle Research, Springer Netherlands, Dordrecht, vol. 20, No. 2, (Feb. 19, 2018), pp. 1-12, XP036434278.

Office Action (Notification of Reason(s) for Refusal) issued on Jul. 29, 2025, in corresponding Japanese Patent Application No. 2022-571677 and machine English translation of the Office Action. (13 pages).

Office Action/Search Report (The First Office Action) issued on Jun. 19, 2025, in corresponding Chinese Patent Application No. 202180072396.9 and machine English translation of the Office Action/Search Report. (17 pages).

Office Action (The Second Office Action) issued on Dec. 30, 2025, in corresponding Chinese Patent Application No. 202180072396.9 and machine English translation of the Office Action. (11 pages).

Office Action (Decision of Refusal and Decision of Dismissal of Amendment) issued on Oct. 21, 2025, in Corresponding Japanese Patent Application No. 2022-571677 and machine English translation of the Office Action. (8 pages).

Office Action (Rejection Decision) issued on Mar. 12, 2026, in corresponding Chinese Patent Application No. 202180072396.9 and machine English translation of the Office Action. (10 pages).

* cited by examiner

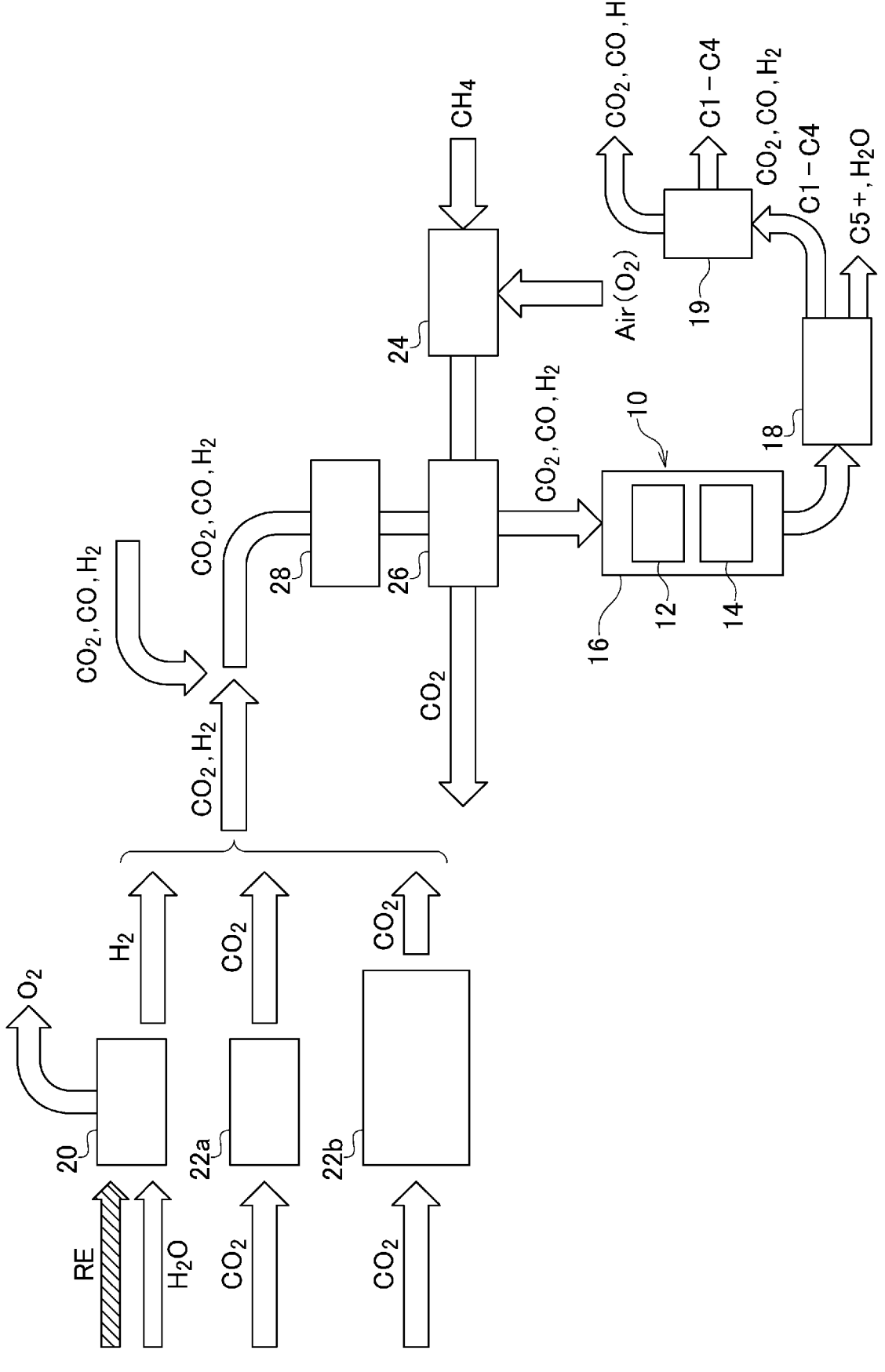

HYDROCARBON PRODUCTION METHOD

CROSS-REFERENCE TO RELATED APPLICATIONS

This application is based upon and claims the benefit of priority from the prior Japanese Patent Application No. 2020-217587, filed on Dec. 25, 2020, and International Patent Application No. PCT/JP2021/048172, filed on Dec. 24, 2021, the entire content of each of which is incorporated herein by reference.

BACKGROUND

Field of the Invention

The present invention relates to a technique for producing hydrocarbon.

Description of the Related Art

As a method for effectively utilizing carbon dioxide contained in exhaust gas or the like, it has been studied to produce liquid hydrocarbon having a high energy density from carbon dioxide and hydrogen in the presence of a catalyst (for example, Patent Literature 1). As a method for producing hydrocarbon using hydrogen and carbon monoxide, Fischer-Tropsch process (hereinafter, appropriately referred to as "FT process".) is known (see Non Patent Literature 1).

In addition, production of a liquid fuel by GTL (Gas to Liquid) using natural gas as a raw material is also known (see Patent Literature 2). The production of a liquid fuel by GTL includes a reforming step of producing hydrogen and carbon monoxide from natural gas, and a synthesis step by FT process of producing higher paraffin using a synthesis gas composed of hydrogen and carbon monoxide as a raw material.

Patent Literature 1: JP 7-80309 A

Patent Literature 2: JP 2008-248179 A

Non Patent Literature 1: Energy & Fuels, Vol. 23, 4190-4195 (2009)

In recent years, reduction of carbon dioxide generated in various economic activities is one of major problems. Therefore, it is required to reduce the use of natural gas, coal, and the like, which are fossil fuels, as much as possible as a fuel used for the production of hydrocarbons.

SUMMARY OF THE INVENTION

The present invention has been made in view of such a situation, and an exemplary object of the present invention is to provide a new technique for reducing fossil fuel-derived materials contained in raw materials used for producing hydrocarbon.

In order to solve the above problems, a hydrocarbon production method of one aspect of the present invention includes a first production step of producing carbon monoxide using carbon dioxide contained in source gas, and a second production step of producing hydrocarbon using hydrogen and carbon monoxide contained in source gas. The source gas contains at least one of carbon dioxide, carbon monoxide, and hydrogen not derived from fossil fuel.

BRIEF DESCRIPTION OF THE DRAWINGS

Embodiments will now be described, by way of example only, with reference to the accompanying drawings which are meant to be exemplary, not limiting, and wherein like elements are numbered alike in several Figures, in which:

FIG. 1 is a schematic diagram showing an outline of a process flow including a hydrocarbon production method according to the present embodiment.

DETAILED DESCRIPTION OF THE INVENTION

First, aspects of the present invention will be listed. A hydrocarbon production method of one aspect of the present invention includes a first production step of producing carbon monoxide using carbon dioxide contained in source gas, and a second production step of producing hydrocarbon using hydrogen contained in source gas and carbon monoxide. The source gas contains at least one of carbon dioxide, carbon monoxide, and hydrogen not derived from fossil fuel.

According to this aspect, it is possible to reduce at least one of carbon dioxide, carbon monoxide, and hydrogen derived from fossil fuel contained in the source gas used for producing hydrocarbon.

The source gas may contain unreacted gas generated in the first production step or the second production step. The unreacted gas is, for example, carbon dioxide, carbon monoxide, hydrogen, or the like.

As a result, the utilization efficiency of the source gas in the first production step or the second production step can be improved.

The source gas may contain hydrogen produced by electrolysis of water using renewable energy. This makes it possible to produce hydrogen while suppressing emission of carbon dioxide.

The source gas may contain carbon dioxide recovered from the atmosphere. As a result, reduction of carbon dioxide in the atmosphere can be expected.

The source gas may contain carbon dioxide recovered from combustion exhaust gas discharged from thermal power generation, a chemical plant, or the like. As a result, reduction of carbon dioxide in the atmosphere can be expected.

The method may further include a hydrocarbon gas separation step of separating a hydrocarbon gas having 4 or less carbon atoms from the hydrocarbon produced in the second production step, a combustion step of combusting the hydrocarbon gas, and a temperature raising step of raising the temperature of the source gas with the combustion exhaust gas produced in the combustion step. The source gas may include carbon dioxide recovered from the combustion exhaust gas. As a result, carbon dioxide released into the atmosphere is reduced. In addition, consumption of fossil fuels for obtaining raw materials can be reduced.

In the first production step, carbon monoxide may be produced by reverse water gas shift (RWGS) reaction.

In the first production step, carbon monoxide may be produced by electrolytic reduction.

In the second production step, hydrocarbon may be produced by a reaction by FT process (Fischer-Tropsch process).

The method may further include a recycled gas separation step of separating at least one of carbon dioxide, carbon monoxide, and hydrogen contained in the gas discharged in the second production step as a recycled gas, and a mixing step of mixing the separated recycled gas with the source gas used in the first production step. As a result, the utilization efficiency of the source gas in the first production step or the second production step can be improved.

In at least one of the hydrocarbon gas separation step and the recycled gas separation step, an object may be separated by at least one method of membrane separation, pressure swing adsorption, or thermal swing adsorption.

The first production step or the second production step may include a reaction that generates water. Water generated by the reaction may be used as a raw material for electrolysis.

Note that arbitrary combinations of the above components and modifications of the expressions of the present invention among methods, apparatuses, systems, and the like are also effective as the aspects of the present invention. In addition, an appropriate combination of the above-described elements can also be included in the scope of the invention for which patent protection is sought by the present patent application.

Hereinafter, the present invention will be described based on preferred embodiments with reference to the drawings. The embodiment is not intended to limit the invention but is an example, and all features described in the embodiment and combinations thereof are not necessarily essential to the invention. The same or equivalent components, members, and processes illustrated in the drawings are denoted by the same reference numerals, and redundant description will be omitted as appropriate. In addition, the scale and shape of each part illustrated in each drawing are set for convenience in order to facilitate the description, and are not limitedly interpreted unless otherwise specified. In addition, even in the case of the same member, scales and the like may be slightly different between the drawings. In addition, when the terms "first", "second", and the like are used in the present specification or claims, unless otherwise specified, they do not represent any order or importance, and are intended to distinguish one configuration from another configuration.

FIG. 1 is a schematic diagram showing an outline of a process flow including a hydrocarbon production method according to the present embodiment. First, an example of a catalyst system for producing hydrocarbon using a reactor according to the present embodiment will be described. A catalyst system 10 shown in FIG. 1 includes a reverse water gas shift reactor 12 disposed upstream, an FT reactor 14 disposed downstream of the reverse water gas shift reactor 12, and a reaction vessel 16 storing the reverse water gas shift reactor 12 and the FT reactor 14.

In the reverse water gas shift reactor 12, a source gas containing hydrogen and carbon dioxide (and carbon monoxide) is introduced from the upstream side, and carbon monoxide is produced from the carbon dioxide by reverse water gas shift reaction using a stored reverse water gas shift catalyst. In other words, the hydrocarbon production method according to the present embodiment includes a step of producing carbon monoxide using carbon dioxide contained in the source gas (first production step). In the first production step, carbon monoxide may be produced by electrolytic reduction.

In the FT reactor 14, a gas containing carbon monoxide produced in the reverse water gas shift reactor 12 and hydrogen is introduced, and a gaseous or liquid hydrocarbon is produced by a reaction by the FT process using a stored FT catalyst. In other words, the hydrocarbon production method according to the present embodiment includes a step of producing hydrocarbon using hydrogen contained in source gas and carbon monoxide (second production step).

The FT reactor 14 produces $CH_4$ and C2-C4 components (for example, methane, ethane, propane, butane) that are gaseous hydrocarbons having 1 to 4 carbon atoms, and a C5+ component (for example, a component having 5 or more carbon atoms in a linear alkane) that is a hydrocarbon having or more carbon atoms and is an oil component that is liquid at normal pressure. A desired component can be extracted by gas-liquid separation and, in some cases, fractionation of the produced gas component and liquid component (moisture and oil) by a gas-liquid separator 18. For example, the liquid component separated by the gas-liquid separator 18 is separated into the C5+ component and water by an oil-water separator.

The gas component separated by the gas-liquid separator 18 is separated into gaseous hydrocarbon (C1 to C4) and a recycled gas containing at least one of unreacted carbon dioxide, carbon monoxide, and hydrogen discharged from the FT reactor 14 by a separator 19. The process of separating the gas components by the gas-liquid separator 18 and separating gaseous hydrocarbons (C1 to C4) from the separated gas components by the separator 19 corresponds to the hydrocarbon gas separation step. Further, the process of separating the gas component by the gas-liquid separator 18 and separating the recycled gas from the gas component by the separator 19 corresponds to the recycled gas separation step. In the present embodiment, the hydrocarbon gas separation step and the recycled gas separation step are described separately. However, the step of separating the hydrocarbon (C1 to C4) from a mixed gas (the gas component produced in the FT reactor 14) of the gaseous hydrocarbon (C1 to C4) and the recycled gas may correspond to the step of separating the recycled gas from the mixed gas. Similarly, the step of separating the recycled gas from the mixed gas may correspond to the step of separating the hydrocarbon (C1 to C4). In this case, the hydrocarbon gas separation step and the recycled gas separation step can also be interpreted as one separation step. The separator 19 may be capable of separating an object by at least one method of membrane separation, pressure swing adsorption, or thermal swing adsorption. The object is a hydrocarbon gas having 4 or less carbon atoms in the case of a hydrocarbon gas separation step, and is a recycled gas in the case of a recycled gas separation step. When the hydrocarbon gas separation step and the recycled gas separation step are performed in different separators, only one of the hydrocarbon gas separation step and the recycled gas separation step may separate the object by any method of membrane separation, pressure swing adsorption, or thermal swing adsorption.

Next, a process for obtaining carbon dioxide, carbon monoxide, and hydrogen contained in the source gas will be described. A hydrogen feeder 20 shown in FIG. 1 produces hydrogen by electrolysis of supplied water using electric power RE derived from renewable energy, and supplies the hydrogen to the downstream side. This makes it possible to produce hydrogen while suppressing the discharge of carbon dioxide, more preferably without discharging carbon dioxide. Also, a carbon dioxide feeder 22a recovers carbon dioxide in the atmosphere by direct air capture (DAC), and supplies the carbon dioxide to the downstream side. As a result, reduction of carbon dioxide in the atmosphere can be expected. Also, a carbon dioxide feeder 22b separates and recovers carbon dioxide contained in combustion exhaust gas described later by chemical adsorption, and supplies the carbon dioxide to the downstream side. As a result, carbon dioxide released into the atmosphere is reduced. In addition, consumption of fossil fuels for obtaining raw materials can be reduced.

Hydrogen and carbon dioxide supplied from the hydrogen feeder 20 and the carbon dioxide feeders 22a and 22b are used as source gases of the catalyst system 10 disposed on the downstream side. In addition, a flow path between the hydrogen feeder 20 and the like and the catalyst system 10 is provided with a merging path for mixing carbon dioxide, carbon monoxide, and hydrogen as the recycled gas separated by the separator 19 with the source gas (mixing step). In other words, the source gas may contain separated recycled gas (unreacted gas). As a result, the utilization efficiency of the source gas in the catalyst system 10 can be improved.

In addition, the source gas used by the catalyst system 10 contains at least one of carbon dioxide, carbon monoxide, and hydrogen that are not derived from fossil fuel. In other words, it is possible to reduce at least one of carbon dioxide, carbon monoxide, and hydrogen derived from fossil fuel contained in the source gas used for producing hydrocarbon.

As described above, the gas-liquid separator 18 and the separator 19 separate the hydrocarbon gas having 4 or less carbon atoms from the hydrocarbon produced in the FT reactor 14 (hydrocarbon gas separation step). Then, the separated hydrocarbon gas (for example, methane) is combusted together with air by a boiler 24 (combustion step), and the high-temperature combustion exhaust gas is sent to a preheater 26. In the preheater 26, heat exchange is performed between the source gas boosted by a pump 28 and the combustion exhaust gas (temperature raising step), the heated source gas is supplied to the catalyst system 10, and the subsequent reaction is performed. The combustion exhaust gas subjected to the heat exchange in the preheater 26 is supplied to the carbon dioxide feeder 22b, and the carbon dioxide is recovered.

The reverse water gas shift reactor 12 and the FT reactor 14 both contain a reaction that generates water. Therefore, water separated by the gas-liquid separator 18 or the subsequent oil-water separator may be used as a raw material for electrolysis in the hydrogen feeder 20.

Next, the reverse water gas shift catalyst used in the reverse water gas shift reactor 12 will be described in detail. The reverse water gas shift catalyst may contain metallic copper or copper oxide (CuO), or both. While the copper-based catalyst functions as a catalyst, the copper-based catalyst contains at least metallic copper. Therefore, the catalyst is subjected to reduction treatment before being used in the reaction. The copper-based catalyst before the reduction treatment often contains copper oxide.

The content of the copper component in the copper-based catalyst is preferably 20 to 100% by mass based on the mass of the entire copper-based catalyst when all the amounts of copper components contained in the copper-based catalyst are converted into the amount of metallic copper.

The copper-based catalyst may further contain zinc oxide (ZnO). The copper-based catalyst contains zinc oxide, whereby liquid hydrocarbon can be more efficiently produced. When the entire amount of the copper element contained in the copper-based catalyst is converted into the amount of copper oxide, the ratio of the amount of zinc oxide is preferably 10 to 70% by mass, and further preferably 20 to 50% by mass, based on the total amount of copper oxide and zinc oxide.

The reverse water gas shift catalyst may contain at least one metal selected from the group consisting of rhodium, platinum, or iron-chromium. By containing these metals, carbon monoxide can be more efficiently produced from carbon dioxide contained in the source gas.

The copper-based catalyst may further contain a carrier that carries a copper component. When the copper-based catalyst contains zinc oxide, zinc oxide is also usually carried by the carrier. The carrier is preferably alumina such as γ-alumina. The content of the carrier in the copper-based catalyst is, for example, 0.5 to 60% by mass, preferably 1 to 50% by mass, and further preferably 1 to 40% by mass, based on the total of the content of copper, the content of zinc oxide, and the content of the carrier (for example, alumina). Here, the content of copper means an amount obtained by converting all the amounts of copper components contained in the copper-based catalyst into the amount of metallic copper.

The copper-based catalyst containing a copper component and zinc oxide can be obtained, for example, by a method including the steps of producing a precipitate containing copper and zinc by coprecipitation method and firing the produced precipitate. The precipitate includes, for example, a hydroxide of copper and zinc, a carbonate, or a composite salt thereof. A copper-based catalyst containing a copper component, zinc oxide and a carrier can be obtained by producing a precipitate containing copper and zinc by coprecipitation method from a solution containing a carrier (for example, alumina).

A fired body formed by firing and containing a copper component and zinc oxide may be pulverized, or a granular molded body may be formed by further molding a powder. Examples of the method for molding a powder include extrusion molding and tablet molding. It is also possible to obtain a molded body by molding a mixture containing the powder of the fired body and carbon black.

Next, details of the FT catalyst used in the FT reactor 14 will be described. The FT catalyst is preferably an iron-based catalyst containing an iron component containing metallic iron, iron oxide, or both of these, and at least one added metal selected from the group consisting of alkali metals or alkaline earth metals. Also, the FT catalyst may be an iron-based catalyst/copper-based catalyst containing a copper component in addition to an iron component. While the iron-based catalyst functions as a catalyst, the iron-based catalyst usually contains at least metallic iron. Therefore, the catalyst is usually subjected to reduction treatment before being used in the reaction. The iron-based catalyst before the reduction treatment usually contains iron oxide (for example, $Fe_3O_4$ or $Fe_2O_3$).

The content of the iron component in the iron-based catalyst is preferably 5 to 100% by mass based on the mass of the entire iron-based catalyst when all the amounts of iron components contained in the iron-based catalyst are converted into the amount of iron oxide.

The added metal contains one or more types arbitrarily selected from alkali metals. For example, the added metal preferably contains at least one selected from the group consisting of sodium, potassium, and cesium. Of course, two or more types of added metals may be used. When the added metal contains sodium, potassium, or cesium, a liquid hydrocarbon can be more efficiently produced.

The content of the added metal in the iron-based catalyst is preferably 0.2 to 40% by mass, and further preferably 0.5 to 20% by mass, based on the amount of a portion other than the added metal in the iron-based catalyst. When the added metal contains sodium, the content of sodium in the iron-based catalyst is preferably 0.2 to 20% by mass, and further preferably 0.5 to 10% by mass. When the added metal contains potassium, the content of potassium in the iron-based catalyst is preferably 0.2 to 40% by mass, and further preferably 0.5 to 20% by mass. When the added metal contains cesium, the content of cesium in the iron-based catalyst is preferably 0.2 to 20% by mass, and further preferably 0.5 to 10% by mass. When the content of the added metal is within the above range, the conversion rate from carbon monoxide to hydrocarbon tends to be further improved.

The iron-based catalyst can be obtained, for example, by a method including the steps of producing a precipitate of a hydroxide containing trivalent iron from an aqueous solution containing Fe 3+, firing the precipitate to form a powder containing ferric oxide, and mixing the powder with an aqueous solution containing an added metal and then drying the aqueous solution containing the added metal.

A powder containing ferric oxide may be further molded to form a granular molded body. Examples of the method for molding a powder include extrusion molding and tablet molding. It is also possible to obtain a molded body by molding a mixture containing the powder of the fired body and carbon black.

Each catalyst may be heated while allowing the reaction for producing hydrocarbon from the source gas to proceed. The heating temperature for the reaction is, for example, 200 to 400° C. Also, the source gas may contain only one of carbon dioxide and carbon monoxide, or may be a mixed gas containing carbon dioxide and carbon monoxide.

Although the present invention has been described with reference to the above-described embodiments, the present invention is not limited to the above-described embodiments, and configurations obtained by appropriately combining or replacing the configurations of the embodiments are also included in the present invention. In addition, it is also possible to appropriately recombine the combinations and the order of processing in the embodiments on the basis of the knowledge of those skilled in the art and to add modifications such as various design changes to the embodiments, and the embodiments to which such modifications are added can also be included in the scope of the present invention.

The invention claimed is:

1. A hydrocarbon production method comprising:
a first production step of producing carbon monoxide using carbon dioxide contained in a source gas;
a second production step of producing hydrocarbon using hydrogen contained in the source gas and the carbon monoxide, wherein the source gas comprises at least one of carbon dioxide, carbon monoxide, and hydrogen that are not derived from fossil fuel;
a hydrocarbon gas separation step of separating a hydrocarbon gas having 4 or less carbon atoms from the hydrocarbon produced in the second production step;
a combustion step of combusting the hydrocarbon gas; and
a temperature raising step of sending to a preheater the combustion exhaust gas produced in the combustion step and raising the temperature of the source gas of the first production step and the second production step by the preheater with the combustion exhaust gas produced in the combustion step,
wherein the source gas used in the first production step and the second production step comprises carbon dioxide recovered from the combustion exhaust gas.

2. The hydrocarbon production method according to claim 1, wherein the source gas used in the first production step and the second production step comprises an unreacted gas generated in the first production step or the second production step.

3. The hydrocarbon production method according to claim 1, wherein the source gas used in the first production step and the second production step comprises hydrogen produced by electrolysis of water using renewable energy.

4. The hydrocarbon production method according to claim 1, wherein the source gas used in the first production step comprises carbon dioxide recovered from the atmosphere.

5. The hydrocarbon production method according to claim 1, wherein the source gas used in the first production step comprises carbon dioxide recovered from combustion exhaust gas.

6. The hydrocarbon production method according to claim 1, wherein the first production step produces carbon monoxide by reverse water gas shift reaction.

7. The hydrocarbon production method according to claim 1, wherein the first production step produces carbon monoxide by electrolytic reduction.

8. The hydrocarbon production method according to claim 1, wherein the second production step produces hydrocarbon by a reaction by FT process (Fischer-Tropsch process).

9. The hydrocarbon production method according to claim 1, further comprising:
a recycled gas separation step of separating at least one of carbon dioxide, carbon monoxide, and hydrogen contained in the gas discharged in the second production step as a recycled gas; and
a mixing step of mixing the separated recycled gas with the source gas used in the first production step.

10. The hydrocarbon production method according to claim 9, comprising a hydrocarbon gas separation step of separating a hydrocarbon gas having 4 or less carbon atoms from the hydrocarbon produced in the second production step,
wherein the hydrocarbon gas separation step separates the hydrocarbon gas by at least one method of membrane separation, pressure swing adsorption, and thermal swing adsorption, or
wherein the recycled gas separation step separates the recycled gas by at least one method of membrane separation, pressure swing adsorption, and thermal swing adsorption, or
wherein the hydrocarbon gas separation step and the recycled gas separation step each separate the hydrocarbon gas and the recycled gas, respectively, by at least one method of membrane separation, pressure swing adsorption, and thermal swing adsorption.

11. The hydrocarbon production method according to claim 3,
wherein the first production step or the second production step includes a reaction that generates water, and
water generated by the reaction is used as a raw material for the electrolysis.

12. The hydrocarbon production method according to claim 1, comprising a recycled gas separation step of separating at least one of carbon dioxide, carbon monoxide, and hydrogen contained in the gas discharged in the second production step as a recycled gas,
wherein the hydrocarbon gas separation step and the recycle gas separation step are performed as one step.

13. The hydrocarbon production method according to claim 6, wherein the reverse shift reaction is carried out using a reverse shift catalyst containing a copper-based catalyst and zinc oxide.

14. The hydrocarbon production method according to claim 13, wherein when the entire amount of the copper element contained in the copper-based catalyst is converted into the amount of copper oxide, the ratio of the amount of zinc oxide is 10 to 70% by mass based on the total amount of copper oxide and zinc oxide.

15. The hydrocarbon production method according to claim 13, wherein the reverse shift catalyst further contains at least one metal selected from the group consisting of rhodium, platinum, or iron-chromium.

16. The hydrocarbon production method according to claim 8, wherein the reaction by FT process is carried out using an FT catalyst comprising an iron-based catalyst containing an iron component and at least one added metal selected from the group consisting of sodium, potassium, and cesium.

17. The hydrocarbon production method according to claim 16, wherein the content of the added metal in the iron-based catalyst is 0.2 to 40% by mass based on the amount of a portion other than the added metal in the iron-based catalyst.

* * * * *